(12) United States Patent
Doppiu et al.

(10) Patent No.: US 10,584,142 B2
(45) Date of Patent: Mar. 10, 2020

(54) PREPARATION OF RHODIUM(III)-2-ETHYLHEXANOATE

(71) Applicant: Umicore AG & Co. KG, Hanau-Wolfgang (DE)

(72) Inventors: Angelino Doppiu, Seligenstadt (DE); Birgit Emrich, Michelstadt (DE); Ralf Karch, Kleinostheim (DE); Andreas Rivas-Nass, Bensheim (DE); Eileen Woerner, Nidderau (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 230 days.

(21) Appl. No.: 15/737,027

(22) PCT Filed: Jul. 1, 2016

(86) PCT No.: PCT/EP2016/065466
§ 371 (c)(1),
(2) Date: Dec. 15, 2017

(87) PCT Pub. No.: WO2017/001647
PCT Pub. Date: Jan. 5, 2017

(65) Prior Publication Data
US 2018/0170952 A1  Jun. 21, 2018

(30) Foreign Application Priority Data

Jul. 2, 2015  (EP) .................... 15175105

(51) Int. Cl.
| C07F 15/00 | (2006.01) |
| C07C 51/41 | (2006.01) |
| C07C 45/50 | (2006.01) |
| B01J 23/46 | (2006.01) |
| C07C 53/128 | (2006.01) |

(52) U.S. Cl.
CPC ........... *C07F 15/008* (2013.01); *B01J 23/464* (2013.01); *C07C 45/50* (2013.01); *C07C 51/412* (2013.01); *C07C 51/418* (2013.01); *C07C 53/128* (2013.01)

(58) Field of Classification Search
None
See application file for complete search history.

(56) References Cited

U.S. PATENT DOCUMENTS

| 4,205,013 | A | 5/1980 | Weber et al. |
| 4,845,306 | A | 7/1989 | Puckette |
| 5,041,675 | A | 8/1991 | Lukas et al. |
| 8,173,847 | B2 | 5/2012 | Fischbach et al. |
| 2009/0171121 | A1 | 7/2009 | Liu et al. |

FOREIGN PATENT DOCUMENTS

| DE | 3822038 A1 | 3/1990 |
| WO | WO-9210460 A1 | 6/1992 |
| WO | WO-2009059713 A1 | 5/2009 |

OTHER PUBLICATIONS

International Search Report for PCT/EP2016/065466 dated Jul. 27, 2016.
Written Opinion of the International Searching Authority for PCT/EP2016/065466 dated Jul. 27, 2016.

*Primary Examiner* — Yun Qian
(74) *Attorney, Agent, or Firm* — Drinker Biddle & Reath LLP

(57) ABSTRACT

The present invention provides a method for preparing rhodium (III) 2-ethylhexanoate solutions which supplies the reaction product with higher space yield, as well as lower sodium and chloride ion content. An aqueous solution of an alkali salt of 2-ethylhexanoate is thereby initially converted with a rhodium (III) precursor. The rhodium (III) precursor is selected from rhodium (III) chloride solution, rhodium (III) chloride hydrate, and rhodium (III) nitrate. The mixture is heated for several hours. After cooling to room temperature, the rhodium (III) 2-ethylhexanoate formed is extracted from the aqueous solution with an alcohol that is immiscible in water or a carboxylic acid that is immiscible in water, and optionally washed with aqueous mineral acid. The rhodium (III) 2-ethylhexanoate solution obtainable in this way may be used directly as catalyst in hydroformylation reactions.

5 Claims, No Drawings

PREPARATION OF RHODIUM(III)-2-ETHYLHEXANOATE

CROSS-REFERENCE TO RELATED APPLICATIONS

This application is a national stage application (under 35 U.S.C. § 371) of PCT/EP2016/065466, filed Jul. 1, 2016, which claims benefit of European Application No. 15175105.4, filed Jul. 2, 2015, both of which are incorporated herein by reference in their entirety.

INTRODUCTION

The subject matter of the invention is a method for preparing rhodium(III) 2-ethylhexanoate solutions. Rhodium(III) 2-ethylhexanoate —Rh[$CH_3(CH_2)_3CH(CH_2CH_3)COO$]$_3$— is also referred to as "Rh(III) 2EH" below. Similarly, 2-ethylhexanoate is referred to as "2-EH."

The method according to the invention is characterized by an improved process execution. It facilitates the preparation of Rh(III) 2EH solutions in high yields and very high quality; the solutions exhibit very high purity. "High purity" in this context means low concentrations of sodium, chloride, and Rh(II) species. The yield is in excess of 99% in relation to the rhodium used. Furthermore, the space yield in the preparation of Rh(III) 2EH in accordance with the method presented here is considerably higher than in the preparation based upon methods known from prior art. This high space yield means that the method according to the invention is economically feasible on an industrial scale. Space yield in this context means the product quantity formed per unit volume in a reactor.

The Rh(III) 2EH solutions according to the invention are particularly suitable as catalysts in hydroformylation reactions.

PRIOR ART

There are two possible structures of rhodium 2-ethylhexanoate:

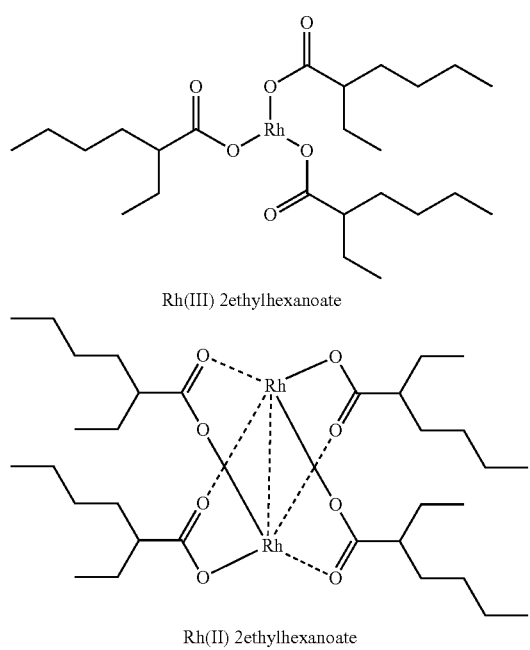

Rh(III) 2ethylhexanoate

Rh(II) 2ethylhexanoate

The structure of the rhodium 2-ethylhexanoate depends upon the oxidation level of the rhodium. The rhodium (II) dimer is green, whereas the rhodium (III) compound is yellowish brown to reddish brown.

Rhodium (III) 2-ethylhexanoate is commercially available under CAS No. 20845-92-5. Rhodium carboxylates are predominantly used in the chemical industry as pre-catalysts for hydroformylation reactions.

Thus, WO 2009/059713 A1 discloses a method for preparing aldehydes by means of the hydroformylation of olefins with carbon monoxide, wherein Rh 2-ethylhexanoate is used as catalyst. Hydroformylation, or oxo reaction, is the transition metal-catalyzed conversion of olefins or olefinic unsaturated compounds with hydrogen and carbon monoxide into aldehydes and alcohols which contain one carbon atom more than the olefin used. The hydroformylation process has meanwhile acquired considerable commercial and technical significance. The aldehydes that are primarily obtained thereby are used as such or represent valuable precursors for producing alcohols, carboxylic acids, esters, or amines, for example.

The hydroformylation is catalyzed by means of hydridometal carbonyls, advantageously those of metals of subgroup VIII of the periodic table of elements. Along with cobalt, the classic catalyst metal, catalysts based upon rhodium have been used increasingly for some years now. In contrast to cobalt, rhodium allows the reaction to be carried out at lower pressure. Furthermore, when terminal olefins are used, linear-chain n-aldehydes are advantageously formed, and iso-aldehydes only to a lesser extent. Ultimately, the hydrogenation of the olefins used into saturated hydrocarbons in the presence of rhodium catalysts is considerably lower than with the application of cobalt catalysts.

Industrially, the hydroformylation of olefinically unsaturated compounds is carried out under the catalytic effect of rhodium carbonyl complexes with tertiary organic phosphines or phosphites as ligands.

According to a further method variant, the rhodium-catalyzed hydroformylation reaction may also be run in the absence of complex-forming ligands—for example, of phosphines or phosphites. Such rhodium catalysts not modified using phosphines or phosphites, and their suitability as hydroformylation catalysts, are known from the literature and are referred to as unmodified rhodium catalysts. In the specialist literature, it is assumed that the rhodium compounds HRh(CO)$_4$ are the catalytically active rhodium species during hydroformylation with unmodified rhodium catalysts, even though this has not been clearly substantiated due to the many chemical reactions running alongside one another in the reaction zone. It is stated that under the conditions of the hydroformylation reaction in the reaction zone, the unmodified rhodium catalysts are formed from rhodium compounds—allegedly rhodium salts such as rhodium (III) chloride, rhodium (III) nitrate, rhodium (III) acetate, rhodium (II) acetate, rhodium (III) sulphate, or rhodium (III) ammonium chloride—from salts of rhodium oxoacids—for example, rhodates—from rhodium carbonyl compounds such as Rh$_4$(CO)$_{12}$ and Rh$_6$(CO)$_{16}$, or from organorhodium compounds such as rhodium carbonyl acetylacetonate, cyclooctadiene rhodium acetate or chloride in the presence of carbon monoxide/hydrogen mixtures, which are also referred to as synthesis gas. The rhodium compound may thereby be used as a solid, or, expediently, in solution. A method for hydroformylation in the presence of unmodified rhodium complexes in which rhodium 2-ethylhexanoate is used is described in DE 38 22 038 A1, for example.

Suitable rhodium compounds which are used in the preparation of the rhodium solution are, for example, salts of aliphatic mono- or polycarboxylic acids with 2 to 13 carbon atoms. Furthermore, carbonyl compounds of rhodium have proved very successful. Although halogen carbonyl compounds may also be used, they have only a limited application due to the corrosive behavior of the halide ions. Ultimately, complex compounds of rhodium—in particular, rhodium (III) compounds—are also suitable starting materials for the preparation of the catalytically active metal components in the catalyst system. These compounds contain monodentate, bidentate or tridentate ligands such as β-diketones—e.g., acetylacetone—or aliphatic and diethylenically unsaturated hydrocarbons such as cyclopentadiene and 1,5-cyclooctadiene. Rhodium compounds which are particularly suitable for the preparation of the rhodium solution are rhodium oxides, rhodium carbonyls, rhodium acetate, rhodium 2-ethylhexanoate, rhodium isononanoate, and rhodium (III) acetylacetonate.

Two methods for preparing rhodium 2-ethylhexanoate are known from prior art.

U.S. Pat. No. 4,845,306 describes a method in which 1.5 equivalent NaOH and 1 equivalent 2-ethylhexanoic acid are dissolved in water in a first vessel. Rhodium chloride hydrate is dissolved in water in a second vessel. 1 equivalent rhodium chloride hydrate solution is added to 7 equivalent sodium 2-ethylhexanoate solution and stirred at 95° C. for two hours. A raw product is formed in the form of a dark green oil. The raw product is then extracted with texanol. In this method, the rhodium concentration is 10,000 ppm in the organic phase and 2 ppm in the combined aqueous phases, such that the yield in relation to the rhodium used is very small. As a result of using a large excess of base, the formation of rhodium hydroxide cannot be avoided. Furthermore, the green color indicates the presence of rhodium (II) 2-ethylhexanoate (Rh(II) 2EH), which is considered less active in catalysis.

WO 92/10460 describes a method in which rhodium trichloride trihydrate is dissolved in ethanol. Sodium 2-ethylhexanoate (Na-2-EH) and ethylhexanoic acid are then added, and the mixture is stirred at room temperature. The ratio of $RhCl_3*3H_2O$ to Na-2-EH is thereby approximately 1:3 (mol/mol). Lastly, the reaction mixture is heated to 40° C. and filtered to separate the NaCl produced. A viscous yellow-green oil is obtained. The yield is hereby 97% in relation to the rhodium used; however, the oil contains high concentrations of sodium and chloride ions and the green color indicates the presence of rhodium (II) 2-ethylhexanoate (Rh(II) 2EH). Due to the use of ethanol as a solvent in basic media, a reduction of the rhodium ions to rhodium metal may take place. For this reason, a complex interim filtration is required to separate off the metal.

A high content of chloride ions in the rhodium (III) 2-ethylhexanoate is disadvantageous, because chloride ions are corrosive and interfere with the catalytic reaction in the hydroformylation by reducing the activity of the catalyst.

For this reason, the object of the invention is to overcome the disadvantages of prior art in the preparation of rhodium (III) 2-ethylhexanoate, and to provide a method that may be carried out on an industrial scale with a high yield and which delivers a reaction product with low sodium and chloride ion content.

BRIEF SUMMARY OF THE INVENTION

This problem is solved by a method for preparing a solution of rhodium (III) 2-ethylhexanoate, comprising the steps a) preparing an aqueous solution of an alkali salt of 2-ethylhexanoate by adding 2-ethylhexanoic acid to an aqueous alkali hydroxide solution at room temperature in a first reaction vessel, wherein the molar ratio of 2-ethylhexanoic acid to alkali hydroxide is 1.0:1.0 to 1.1:1.0 (mol/mol), b) providing a rhodium (III) precursor, selected from rhodium (III) chloride hydrate $RhCl_3*xH_2O$, rhodium (III) chloride solution $H_3[RhCl_6]*(H_2O)_n$, and rhodium (III) nitrate solution $Rh(NO_3)_3*(H_2O)_n$, as well as mixtures thereof, in a second reaction vessel, c) mixing the aqueous solution of the alkali salt of 2-ethylhexanoate and the aqueous solution of the rhodium (III) precursor at an internal temperature of 20-30° C. in the reaction vessel d) heating the mixture from step c)
to an internal temperature of 80-90° C. in the reaction vessel, if the Rh(III) precursor is Rh(III) chloride solution or Rh(III) chloride hydrate, or
to an internal temperature of 80-100° C., if the Rh(III) precursor is Rh(III) nitrate, e) cooling the suspension from step d) while stirring
to an internal temperature of 40-50° C., if the Rh(III) precursor is Rh(III) chloride solution or Rh(III) chloride hydrate, or
to an internal temperature of 55-65° C., if the Rh(III) precursor is Rh(III) nitrate f) adding an alcohol that is immiscible with water, a carboxylic acid that is immiscible with water, or a mixture thereof, while stirring, g) stirring afterward for 30 min. to 3 h, h) cooling to room temperature and leaving the emulsion to settle, i) draining off the lower, Rh-free aqueous phase, j) washing of the organic phase containing Rh-2-EH with aqueous mineral acid, if the Rh(III) precursor in the step contains rhodium (III) chloride hydrate $RhCl_3*xH_2O$ and/or rhodium (III) chloride solution $H_3[RhCl_6]*(H_2O)_n$.

DETAILED DESCRIPTION OF THE INVENTION

The solution of the problem comprises the provision of a method for the preparation of rhodium (III) 2-ethylhexanoate. The method is environmentally friendly and economical due to the chemicals used, the process method, the high product quality, and the high yields achievable, as well as the space yield.

The method comprises the preparation of rhodium (III) 2-ethylhexanoate without any isolation of intermediates. The present invention, therefore, describes a process in which the target product is prepared from the starting materials, without costly and time-consuming intermediate isolation or intermediate washing.

The method provides the reaction product rhodium (III) 2-ethylhexanoate in the form of a solution which may be used directly in other reactions in which Rh(III) 2-EH should act as catalyst. Therefore, no costly and time-consuming isolation is required—for example, due to concentrating the solution or producing solid Rh(III) 2-EH. The Rh(III) 2-EH solution prepared using the method according to the invention is essentially free of Rh(II) 2-ethylhexanoate.

The method according to the invention for the preparation of rhodium (III) 2-ethylhexanoate is explained below, wherein the invention comprises all embodiments listed below individually and in combination with one another.

In step a) of the method according to the invention, an aqueous solution of an alkali salt of 2-ethylhexanoate is prepared by adding 2-ethylhexanoic acid to an aqueous alkali hydroxide solution at room temperature while stirring. The molar ratio of 2-ethylhexanoic acid to alkali hydroxide is thereby 1:1 to 1.1 to 1 (mol/mol). For the concentration of the aqueous alkali hydroxide solution, 1 to 6 mol/l have been found to be practical. In a specific embodiment, this aqueous alkali hydroxide solution is prepared using demineralized water. Suitable alkali hydroxides are LiOH, NaOH, and KOH. NaOH is advantageously used.

In step b) of the method according to the invention, a rhodium (III) precursor is provided. The rhodium (III) precursor is selected from rhodium (III) chloride hydrate $RhCl_3*xH_2O$, rhodium (III) chloride solution $H_3[RhCl_6]*(H_2O)_n$, and rhodium (III) nitrate solution $Rh(NO_3)_3*2H_2O$, as well as mixtures thereof. Optionally, the rhodium (III) precursor may be diluted with water in step b) of the method according to the invention.

It is known to the person skilled in the art that the Rh(III) chloride hydrate and Rh(III) chloride solution are not defined compounds with an exact stoichiometric composition. Therefore, formulas $RhCl_3*xH_2O$, and $H_3[RhCl_6]*(H_2O)_n$ represent idealized compositions. The present complex compounds change, depending upon the halide and water content of the compounds. Rhodium (III) chloride hydrate and its commercially available aqueous solution are normally present as mixed chloro-aquo complexes, which is why the water content in the idealized formula is given as "$xH_2O$". Depending upon the production process for rhodium (III) chloride hydrate and rhodium (III) chloride solution, more or fewer aquo or chloride ligands are bound to the rhodium (III) complex. In the production of a solid of Rh(III) chloride hydrate, this depends upon the degree of evaporation, and, in the production of a solution, upon the acid content (HCl) and the concentration of this solution.

The Rh(III) precursors, rhodium (III) chloride hydrate $RhCl_3*xH_2O$, and rhodium (III) chloride solution $H_3[RhCl_6]*(H_2O)_n$ to be used according to the invention are commercially available. Generally, all rhodium (III) chloride hydrates and rhodium (III) chloride solutions can be used for the method according to the invention, independently of their respective water or chloride content (Rh/Cl-ratio), provided that these rhodium (III) chloride hydrates and rhodium (III) chloride are completely soluble in water. In the context of the present invention, "completely soluble in water" means that at least 100 g of the corresponding rhodium compound are soluble in one liter (1000 mL) of water at room temperature.

In one embodiment, the Rh(III) precursor is a Rh(III) chloride precursor. It is selected from a rhodium (III) chloride hydrate with a maximum rhodium content of 40% and rhodium (III) chloride solutions with a rhodium content of approx. 20% and a chlorine/rhodium ratio of 4:1 to 6:1.

It is particularly advantageous if the Rh(III) chloride precursor is $H_3[RhCl_6]*n(H_2O)$, which is referred to below as "rhodium (III) chloride solution." Typically, aqueous rhodium (III) chloride solutions with a rhodium content of less than 30 wt % are used as they are available commercially and produced—for example, by dissolving rhodium metal in the presence of concentrated hydrochloric acid and chlorine gas. However, suitable rhodium (III) chloride solutions may also be diverted from process streams in precious metal recycling or in industrial precious metal chemistry. Furthermore, the use of a rhodium (III) chloride solution, in comparison to the commonly used solid rhodium (III) chloride hydrate, has the advantage of offering more cost-effective and faster processing, since upstream evaporation, isolation as rhodium (III) chloride hydrate, and analysis to determine the starting quantity are not required.

In a further embodiment, the Rh(III)chloride precursor is rhodium (III) chloride hydrate $RhCl_3*xH_2O$. It is known to the person skilled in the art that this substance is a solid.

In a further embodiment, the Rh(III) precursor is a Rh(III) nitrate solution with a maximum rhodium content of 15 wt % and a chloride content of <0.1 wt %. These types of Rh(III) nitrate solutions are commercially available. Alternatively, the rhodium nitrate solution may itself be prepared by converting freshly prepared Rh(III) hydroxide with nitric acid into Rh(III) nitrate according to the reaction equations

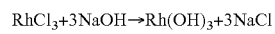

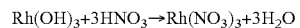

An aqueous solution of $Rh(NO_3)_3$ is obtained. This method for preparing Rh(III) nitrate is known to the person skilled in the art.

The rhodium (III) nitrate to be used according to the invention is also completely water-soluble within the meaning of the above definition.

As mentioned above, rhodium (III) chloride solution and rhodium (III) nitrate are present as aqueous solutions. In contrast, rhodium (III) chloride hydrate is a solid. All three rhodium (III) precursors referred to may be used in step b) of the method according to the invention either without the further addition of water or diluted with water, or—in the case of the rhodium (III) chloride hydrate—dissolved in water. Deionized water, also referred to below as "DI water," is advantageously used to dissolve or dilute the rhodium (III) precursors. Of course, demineralized water or distilled water are suitable as well.

In a specific embodiment, an aqueous solution of the Rh(III) precursor with a pure rhodium concentration of 15-30 g/L—advantageously, 20-25 g/L—is prepared in step b).

In step c) of the method according to the invention, the solution of the alkali salt of 2-ethylhexanoate from step a) is mixed with the aqueous solution of an Rh(III) precursor from step b) at an internal temperature of the reaction vessel of 20-30° C., while stirring. In so doing, the alkali salt of 2-ethylhexanoate (2-EH) and Rh(III) precursor are advantageously mixed together in a ratio of 2:1 to 8:1 (mol/mol) with respect to the amounts of ethylhexanoate and pure rhodium.

In a specific embodiment, the Rh(III) precursor is rhodium (III) chloride solution or rhodium (III) chloride hydrate, and the ratio of 2-EH to Rh(III) precursor is 6:1 to 8:1 mol/mol.

In a further specific embodiment, the Rh(III) precursor is rhodium (III) nitrate, and the ratio of 2-EH to Rh(III) precursor is 2:1 to 5:1 mol/mol.

The 2-EH solution and Rh(III) precursor solution may be mixed continuously or discontinuously. Continuous mixing means that the 2-EH solution and Rh(III) precursor solution are introduced into a mixing vessel simultaneously. Discontinuous mixing means that one mixing component is first introduced completely, and, then, the other mixing component is added.

In a specific embodiment, the Rh(III) precursor solution is introduced, and, then, the alkali 2-EH solution is added.

In another advantageous embodiment, the alkali 2-EH solution is introduced, and, then, the Rh(III) precursor solution is provided.

Once the mixing of the solutions of 2-EH and Rh(III) precursor has ended, in accordance with step d) of the method according to the invention, while stirring,
- it is heated to an internal temperature of 80-90° C. in the reaction vessel, if the Rh(III) precursor is Rh(III) chloride solution or Rh(III) chloride hydrate, or
- it is heated to an internal temperature of 80-100° C., if the Rh(III) precursor is Rh(III) nitrate;

and stirred for 1 to 4 hours at this temperature. Advantageously, it is stirred for 2 to 3 hours.

The suspension is then cooled while stirring in accordance with step e) of the method according to the invention, and, indeed,
- to an internal temperature of 40-50° C.—more specifically 45° C.—if the Rh(III) precursor is Rh(III) chloride solution or Rh(III) chloride hydrate, or
- to an internal temperature of 55-65° C.—more specifically 60° C.—if the Rh(III) precursor is Rh(III) nitrate.

Thereafter, in accordance with step f) of the method according to the invention, an alcohol that is immiscible with water or a carboxylic acid that is immiscible with water, or mixtures thereof, are added while stirring. The internal temperature is thereby 40-50° C., if rhodium (III) chloride hydrate or rhodium (III) chloride solution was used as Rh(III) precursor, and 60-70° C., if rhodium (III) nitrate was used as Rh(III) precursor.

Within the scope of the present invention, alcohols and carboxylic acids are referred to as "immiscible with water" if their solubility in water at 20° C. is less than or equal to 50 g/l.

Suitable alcohols are saturated aliphatic, aromatic, and araliphatic alcohols with 5 to 12 carbon atoms which are liquid at room temperature, such as, for example, pentan-1-ol, pentan-2-ol, pentan-3-ol, 2-methylbutan-1-ol, 3-methylbutan-1-ol, 2-methylbutan-2-ol, 3-methylbutan-2-ol, 2,2-dimethylpropan-1-ol, hexan-1-ol, heptan-1-ol, octan-1-ol, 2,4,4-trimethylpentanol, nonan-1-ol, 3,3,5-trimethylhexanol, 3,5,5-trimethylhexanol, decan-1-ol, undecan-1-ol, dodecan-1-ol, pentan-1,5-diol, pentan-1,5-diol, 1,2,3-propantriol, cyclopentanol, phenylmethanol, 1-phenylethan-1-ol, 2-phenylethan-1-ol, texanol, and 2,2,4-trimethyl-1,3-pentandiol monoisobutyrate. Texanol is 2,2,4-trimethyl-1,3-pentandiol monoisobutyrate. Mixtures of these alcohols may also be used.

Suitable carboxylic acids are saturated carboxylic acids with 5 to 13 carbon atoms which are liquid at room temperature. N-valeric acid, 2-methylbutanoic acid, n-caproic acid, n-heptanoic acid, n-octanoic acid, 2-ethylhexanoic acid, n-nonanoic acid, isononanoic acid, and isotridecanoic acid are referred to as examples. The designations, isononanoic acid and isotridecanoic acid, mean the reaction products of the diisobutylene or of the tetrapropylene obtained via hydroformylation and subsequent oxidation.

"An alcohol or a carboxylic acid, or mixtures thereof," means here that
- a single alcohol or
- a single carboxylic acid or
- a mixture of several alcohols or
- a mixture of several carboxylic acids or
- a mixture of at least one alcohol and at least one carboxylic acid may be used. In principle, this means such alcohols and carboxylic acids that are immiscible with water in accordance with the above definition.

In a specific embodiment, the alcohol or the carboxylic acid is selected from 2-ethylhexanol, 2-ethylhexanoic acid, and texanol, wherein a single one of these compounds is used in each case.

The alcohol or the carboxylic acid, or the mixture thereof, serves to extract the formed rhodium (III) 2-ethylhexanoate from the suspension formed in step e). During the extraction performed in step f), rhodium (III) 2-ethylhexanoate transitions essentially quantitatively into the organic phase. The amount of alcohol or carboxylic acid, or of the mixture, is freely selectable within wide ranges. It is advantageously selected such that the concentration of rhodium (III) 2-ethylhexanoate in this organic phase is approximately the same or somewhat higher than the concentration of rhodium (III) 2-ethylhexanoate that should be obtained after complete implementation of the method according to the invention. The method according to the invention provides ready-to-use solutions of rhodium (III) 2-ethylhexanoate in an alcohol, a carboxylic acid, or mixtures thereof, and these ready-to-use solutions may be used directly as catalyst solutions—for example, as catalyst solutions in hydroformylation reactions. If the concentration of rhodium 2EH in the organic phase in accordance with step f) is somewhat higher than it should be after complete implementation of the method according to the invention, it may be diluted accordingly before being used as catalyst solution. Advantageously, the same alcohol or the same carboxylic acid, or the same mixture thereof, is used here as is used in step f).

If the Rh(III) precursor used is rhodium (III) chloride solution or rhodium (III) chloride hydrate, in accordance with step d) of the method according to the invention, the temperature must not exceed 90° C.—and, in steps e) and f), 50° C.—since otherwise a mixture of rhodium (III) 2-ethylhexanoate and rhodium (II) 2-ethylhexanoate is formed. Rhodium (II) 2-ethylhexanoate is also referred to below as Rh(II) 2EH. During the formation of Rh(II) 2EH, green product solutions are formed. This is shown in comparative examples 1 through 3.

However, if the Rh(III) precursor used is rhodium (III) nitrate, the temperature in step d) of the method according to the invention may be up to 100° C.—and, in steps e) and f), up to 65° C.—without Rh(II) 2-EH being formed.

The reaction mixture from step f) is now stirred again in accordance with step g) for 30 min. to 3 h—advantageously, for 1 to 2 h—at the same internal temperature.

In accordance with step h) of the method according to the invention, the reaction mixture is then cooled to an internal temperature of 20-30° C. The stirring of the emulsion is stopped, and the emulsion formed is allowed to settle, wherein phase separation occurs. Settling, advantageously, takes place over a period of one to four hours.

The bottom aqueous phase is then drained off and discarded (step i).

If rhodium (III) chloride hydrate $RhCl_3*xH_2O$ and/or rhodium (III) chloride solution $H_3[RhCl_6]*(H_2O)_n$ is used as Rh(III) precursor, the organic phase is subsequently washed chlorine-free with aqueous mineral acids. Suitable mineral acids are halide-free acids, such as, for example, sulfuric acid, nitric acid, and phosphoric acid. Advantageously, a 0.5-2% aqueous mineral acid solution is used—advantageously, in particular, a 0.5-2% aqueous sulfuric acid solution. It is recommended that, for each washing stage, approximately as much mineral acid solution be used as corresponds to the sum of the volumes of the aqueous solution of the alkali salt of 2-EH and the aqueous solution of the Rh(III) precursor. After each addition of mineral acid, stirring takes place for 2-6 hours at room temperature, the emulsion is subsequently left to settle for 2-6 hours, and, then, the bottom aqueous phase is drained off and discarded. It is advantageous to repeat this wash step once or twice.

The method provides rhodium (III) 2-ethylhexanoate solutions in a yield of 99% metal, based on the metal ("metal yield"), depending upon the rhodium (III) precursor used. The solutions of Rh(III) 2EH obtained are essentially free of Rh(II) species. This can be seen in the color of the solutions according to the invention: Rhodium (III) 2-ethylhexanoate solutions have a yellowish brown color, whereas rhodium (II) 2-ethylhexanoate solutions are green. Some of the methods for preparing rhodium (III) 2-ethylhexanoate that are cited in prior art provide a product that contains a significant proportion of rhodium (II) 2-ethylhexanoate. However, the catalytic effect of Rh(II) 2-EH in hydroformylation reactions is worse than that of Rh(III) 2EH. For this reason, in hydroformylation reactions, it is advantageous to use rhodium 2-ethylhexanoate that consists almost completely of Rh(III) 2-EH and contains, if possible, no Rh(II) 2EH.

UV/VIS spectroscopy may be used to investigate whether the solution obtained by means of the method according to the invention actually is essentially free of Rh(II) 2EH. The solution obtained after performing step i) is measured, if Rh(III) nitrate solution was used as Rh(III) precursor, or the solution obtained after performing step j), if Rh(III) chloride solution or Rh(III) chloride hydrate was used as Rh(III) precursor. In both cases, for measurement by means of UV/VIS spectroscopy, a solution with a rhodium concentration of 1.9-2.1 wt % is measured. It is known to the person skilled in the art that the rhodium content may be determined by means of MS-ICP. Should the rhodium content be higher than 1.9-2.1 wt %, the solution is adjusted accordingly, beforehand. Suitable solvents for the adjustment are the above mentioned carboxylic acids and alcohols. Advantageously, the same carboxylic acid, the same alcohol, or the same mixture is used for the adjustment as was used in step f) of the method according to the invention.

The solution with a rhodium content of 1.9-2.1 wt % is measured in 2 mm QS cuvettes at 597 nm by means of UV/VIS spectroscopy. If the intensity of the absorption bands is less than or equal to 0.350, the rhodium (III) 2-EH solution is then "essentially free of Rh(II) 2EH" within the meaning of the present invention.

The sodium content of the Rh(III) 2-EH solutions according to the invention is below 500 ppm, and the total chlorine content below 2,500 ppm, if rhodium (III) chloride hydrate and/or rhodium (III) chloride solution is used as Rh(III) precursor. If rhodium (III) nitrate is used as Rh(III) precursor, the sodium content of the Rh(III) 2EH solution obtained in accordance with the method according to the invention is below 250 ppm, and the chloride content is below 250 ppm. The specified ppm values thereby refer to the rhodium content.

The rhodium (III) 2-ethylhexanoate is suitable to be used as catalyst in hydroformylation reactions. Such methods are known in the prior art and can in general be described as a method for hydroformylation reactions comprising the steps of
  providing rhodium (III) 2-ethylhexanoate or a solution thereof according to any of claims 1 to 5;
  employing the rhodium (III) 2-ethylhexanoate or its solution so obtained as a catalyst in the hydroformylation reaction.

EXAMPLES

Below, "deionized water" is referred to as "DI water."

Example 1: Preparation of Rhodium (III) 2-Ethylhexanoate in 2-Ethylhexanol from Rh-Chloride Solution at 85° C.

19.3 g sodium hydroxide (6.4 eq., 99%, Merck) are dissolved in 100 mL DI water while stirring. After cooling to room temperature, 71 g 2-ethylhexanoic acid (98%, Oxea) are slowly added drop by drop.

Meanwhile, 7.7 g Rh in the form of approx. 39 g Rh(III) chloride solution (Umicore Product No. 68.2565.2720; Rh content 19.69 wt %, Cl/Rh=4.86) are diluted in 350 mL DI water in a 1 L double jacket reactor while stirring.

The sodium ethylhexanoate solution is added to the Rh-chloride solution at room temperature within 15 minutes by means of a dropping funnel. The reaction mixture is then heated to $T_{internal}$: 85° C. and maintained at this temperature for 3 hours. At the end of the 3 hours, the reaction mixture is cooled to $T_{internal}$: 45° C. At this temperature, 312 g 2-ethylhexanol (98%, Biesterfeld) are added by means of a dropping funnel. The now brown-yellow emulsion is then stirred again for 2 hours and subsequently cooled to 25° C. The agitator is then switched off and the emulsion left to settle for one hour. Phase separation occurs. The bottom, colorless aqueous phase is drained off. 400 mL of an aqueous 0.7% $H_2SO_4$ solution are added to the organic phase and the emulsion stirred for 4 hours. After 4 h, the agitator is switched off, and phase separation occurs again within 1 hour. The aqueous phase is then drained off. The wash step is repeated again.

A clear, yellow-brown product solution with approx. 2% Rh in 99% metal yield is obtained.

The overall chlorine content is determined by means of a chlorine analyzer and is 1350 ppm (in relation to rhodium). The sodium content is determined per ICP-OES, the sodium content is <500 ppm (in relation to rhodium). The UV/VIS spectrum indicates an absorption band of 0.242 intensity at 597 nm.

Example 2: Preparation of Rhodium (III) 2-Ethylhexanoate in 2-Ethylhexanoic Acid from Rh-Chloride Solution at 85° C.

19.3 g sodium hydroxide (99%, Merck) are dissolved in 100 mL DI water while stirring. After cooling to room temperature, 71 g 2-ethylhexanoic acid (98%, Oxea) are slowly added drop by drop.

Meanwhile, 7.7 g Rh in the form of approx. 42 g Rh(III) chloride solution (Umicore Product No. 68.2565.2720; Rh content 18.39 wt %, Cl/Rh=4.93) are diluted in 350 mL DI water in a 1 L double jacket reactor while stirring.

The sodium ethylhexanoate solution is added to the Rh-chloride solution at room temperature within 15 minutes by means of a dropping funnel. The reaction mixture is heated to $T_{internal}$: 85° C. and maintained at this temperature for 3 hours. At the end of the 3 hours, the reaction mixture is cooled to $T_{internal}$: 45° C. At this temperature, 318 g 2-ethylhexanoic acid (98%, Oxea) are added by means of a dropping funnel. The now brown-yellow emulsion is then stirred again for 2 hours and subsequently cooled to 25° C. The agitator is then switched off and the emulsion left to settle for one hour. Phase separation occurs. The bottom aqueous phase is drained off. 400 mL of an aqueous 0.7% $H_2SO_4$ solution are added to the organic phase and the emulsion stirred for 4 hours. After 4 h, the agitator is switched off, and phase separation occurs again within 1 hour. The aqueous phase is then drained off. The wash step is repeated again.

A clear, yellow-brown product solution with approx. 2% Rh in 99% yield is obtained.

The overall chlorine content is determined by means of a chlorine analyzer and is 2100 ppm (in relation to rhodium). The sodium content is determined per ICP-OES; the sodium content is <500 ppm (in relation to rhodium). The UV/VIS spectrum indicates an absorption band of 0.258 intensity at 597 nm.

Example 3: Preparation of Rhodium (III) 2-Ethylhexanoate in Texanol from Rh-Chloride Solution at 85° C.

19.3 g sodium hydroxide (99%, Merck) are dissolved in 100 mL DI water while stirring. After cooling to room temperature, 71 g 2-ethylhexanoic acid (98%, Oxea) are slowly added drop by drop.

Meanwhile, 7.7 g Rh in the form of 43 g Rh(III) chloride solution (Umicore Product No. 68.2565.2720; Rh content 17.83 wt %, Cl/Rh=4.99) are diluted in 350 mL DI water in a 1 L double jacket reactor while stirring.

The sodium ethylhexanoate solution is added to the Rh-chloride solution at room temperature within 15 minutes by means of a dropping funnel. The reaction mixture is heated to $T_{internal}$: 85° C. and maintained at this temperature for 3 hours. At the end of the 3 hours, the reaction mixture is cooled to $T_{internal}$: 45° C. At this temperature, 357 g texanol (99%, 2,2,4-trimethyl-1,3-pentanediol monoisobutyrate, Sigma Aldrich) are added by means of a dropping funnel. The now brown-yellow emulsion is then stirred again for 2 hours and subsequently cooled to 25° C. The agitator is then switched off and the emulsion left to settle for one hour. Phase separation occurs. The bottom aqueous phase is drained off. 400 mL of an aqueous 0.7% $H_2SO_4$ solution are added to the organic phase and the emulsion stirred for 4 hours. After 4 h, the agitator is switched off, and phase separation occurs again within 1 hour. The aqueous phase is then drained off. The wash step is repeated again.

A clear yellow-brown product solution with approx. 2% Rh in 99% yield is obtained.

The overall chlorine content is determined by means of a chlorine analyzer and is 2300 ppm (in relation to rhodium). The sodium content is determined per ICP-OES; the sodium content is <500 ppm (in relation to rhodium). The UV/VIS spectrum indicates an absorption band of 0.324 intensity at 597 nm.

Example 4: Preparation of Rhodium (III) 2-Ethylhexanoate in 2-Ethylhexanol from Rh-Nitrate Solution at 85° C.

11 g sodium hydroxide (99%, Merck) are dissolved in 150 mL DI water while stirring. After cooling to room temperature, 40 g 2-ethylhexanoic acid (98%, Oxea) are slowly added drop by drop.

Meanwhile, 9.0 g Rh in the form of approx. 90 g Rh(III) nitrate solution (Umicore Product No. 68.2565.2810; Rh content 10 wt %, free $HNO_3$/Rh ratio<2, Cl content<0.1%) are diluted in 150 mL DI water in a 1 L double jacket reactor while stirring.

The sodium ethylhexanoate solution is added to the Rh-nitrate solution at 80° C. by means of a dropping funnel within 15 minutes. The reaction mixture is then heated to $T_{internal}$: 85° C. and maintained at this temperature for 2 hours. At the end of the 2 hours, the reaction mixture is cooled to $T_{internal}$: 60° C. At this temperature, 400 g 2-ethylhexanol (98%, Biesterfeld) are added by means of a dropping funnel. The now brown-yellow emulsion is then stirred again for 1 hour and subsequently cooled to 25° C. The agitator is then switched off and the emulsion left to settle for three hours. Phase separation occurs. The bottom, colorless aqueous phase is drained off.

A clear, yellow-brown product solution with approx. 2% Rh in 99% metal yield is obtained.

The overall chlorine content is determined by means of a chlorine analyzer and is 1290 ppm (in relation to rhodium). The sodium content is determined per ICP-OES; the sodium content is <500 ppm (in relation to rhodium). The UV/VIS spectrum indicates an absorption band of 0.085 intensity at 597 nm.

Example 5: Preparation of Rhodium (III) 2-Ethylhexanoate in 2-Ethylhexanol from Rh-Nitrate Solution at 95° C.

11 g sodium hydroxide (99%, Merck) are dissolved in 150 mL DI water while stirring. After cooling to room temperature, 40 g 2-ethylhexanoic acid (98%, Oxea) are slowly added drop by drop.

Meanwhile, 9 g Rh in the form of approx. 90 g Rh(III) nitrate solution (Umicore Product No. 68.2565.2810; Rh content 10 wt %, free $HNO_3$/Rh ratio<2, Cl content<0.1%) are diluted in 150 mL DI water in a 1 L double jacket reactor while stirring.

The sodium ethylhexanoate solution is added to the Rh-nitrate solution at 80° C. within 15 minutes by means of a dropping funnel. The reaction mixture is then heated to $T_{internal}$: 95° C. and maintained at this temperature for 2 hours. At the end of 3 hours, the reaction mixture is cooled to $T_{internal}$: 60° C. At this temperature, 400 g 2-ethylhexanol (98%, Biesterfeld) are added by means of a dropping funnel. The now brown-yellow emulsion is then stirred again for 1 hour and subsequently cooled to 25° C. The agitator is then switched off and the emulsion left to settle for three hours. Phase separation occurs. The bottom aqueous phase is drained off.

A clear, yellow-brown product solution with approx. 2% Rh in 99% metal yield is obtained.

The overall chlorine content is determined by means of a chlorine analyzer and is 1110 ppm (in relation to rhodium). The sodium content is determined per ICP-OES; the sodium content is <500 ppm (in relation to rhodium). The UV/VIS spectrum indicates an absorption band of 0.093 intensity at 597 nm.

Comparative Example 1: Preparation of Rhodium (III) 2-Ethylhexanoate in 2-Ethylhexanol from Rh-Chloride Solution at 95° C.

19.3 g sodium hydroxide (99%, Merck) are dissolved in 100 mL DI water while stirring. After cooling to room temperature, 71 g 2-ethylhexanoic acid (98%, Oxea) are slowly added drop by drop.

Meanwhile, 7.7 g Rh in the form of approx. 39.6 g Rh(III) chloride solution (Umicore Product No. 68.2565.2720; Rh content 19.40 wt %, Cl/Rh=4.74) are diluted in 350 mL DI water in a 1 L double jacket reactor while stirring.

The sodium ethylhexanoate solution is added to the Rh-chloride solution at room temperature within 15 minutes by means of a dropping funnel. The reaction mixture is heated to T$_{internal}$: 95° C. and maintained at this temperature for 3 hours. At the end of the 3 hours, the reaction mixture is cooled to T$_{internal}$: 45° C. At this temperature, 312 g 2-ethylhexanol (98%, Biesterfeld) are added by means of a dropping funnel. The now green-yellow emulsion is then stirred again for 2 hours and subsequently cooled to 25° C. The agitator is then switched off and the emulsion left to settle for one hour. Phase separation occurs. The bottom aqueous phase is drained off. 400 mL of an aqueous 0.7% H$_2$SO$_4$ solution are added to the organic phase and the emulsion stirred for 4 hours. After 4 h, the agitator is switched off, and phase separation occurs again within 1 hour. The aqueous phase is then drained off. The wash step is repeated again.

A clear, dark green product solution with approx. 2% Rh in 99% metal yield is obtained.

The overall chlorine content is determined by means of a chlorine analyzer and is 1090 ppm (in relation to rhodium). The sodium content is determined per ICP-OES; the sodium content is <500 ppm (in relation to rhodium). The UV/VIS spectrum indicates an absorption band of 0.465 intensity at 597 nm.

Comparative Example 2: Preparation of Rhodium (III) 2-Ethylhexanoate in 2-Ethylhexanoic Acid from Rh-Chloride Solution at 95° C.

19.3 g sodium hydroxide (99%, Merck) are dissolved in 100 mL DI water while stirring. After cooling to room temperature, 71 g 2-ethylhexanoic acid (98%, Oxea) are slowly added drop by drop.

Meanwhile, 7.7 g Rh in the form of 40 g Rh(III) chloride solution (Umicore Product No. 68.2565.2720; Rh content 19.28 wt %, Cl/Rh=4.88) are diluted in 350 mL DI water in a 1 L double jacket reactor while stirring.

The sodium ethylhexanoate solution is added to the Rh-chloride solution at room temperature by means of a dropping funnel within 15 minutes. The reaction mixture is heated to T$_{internal}$: 95° C. and maintained at this temperature for 3 hours. At the end of the 3 hours, the reaction mixture is cooled to T$_{internal}$: 45° C. At this temperature, 318 g 2-ethylhexanoic acid (98%, Oxea) are added by means of a dropping funnel. The now greenish emulsion is then stirred again for 2 hours and subsequently cooled to 25° C. The agitator is then switched off and the emulsion left to settle for one hour. Phase separation occurs. The bottom aqueous phase is drained off. 400 mL of an aqueous 0.7% H$_2$SO$_4$ solution are added to the organic phase and the emulsion stirred for 4 hours. After 4 h, the agitator is switched off, and phase separation occurs again within 1 hour. The aqueous phase is then drained off. The wash step is repeated again.

A clear, dark green product solution with approx. 2% Rh in 99% yield is obtained.

The overall chlorine content is determined by means of a chlorine analyzer and is 2450 ppm (in relation to rhodium). The sodium content is determined per ICP-OES; the sodium content is <500 ppm (in relation to rhodium). The UV/VIS spectrum indicates an absorption band of 0.526 intensity at 597 nm.

Comparative Example 3: Preparation of Rhodium (III) 2-Ethylhexanoate in Texanol from Rh-Chloride Solution at 95° C.

19.3 g sodium hydroxide (99%, Merck) are dissolved in 100 mL DI water while stirring. After cooling to room temperature, 71 g 2-ethylhexanoic acid (98%, Oxea) are slowly added drop by drop.

Meanwhile, 7.7 g Rh in the form of approx. 39 g Rh(III) chloride solution (Umicore Product No. 68.2565.2720; Rh content 19.67 wt %, Cl/Rh=4.99) are diluted in 350 mL DI water in a 1 L double jacket reactor while stirring.

The sodium ethylhexanoate solution is added to the Rh-chloride solution at room temperature within 15 minutes by means of a dropping funnel. The reaction mixture is heated to T$_{internal}$: 95° C. and maintained at this temperature for 3 hours. At the end of the 3 hours, the reaction mixture is cooled to T$_{internal}$: 45° C. At this temperature, 357 g texanol (99%, 2,2,4-trimethyl-1,3-pentanediol monoisobutyrate, Sigma Aldrich) are added by means of a dropping funnel. The now greenish emulsion is then stirred again for 2 hours and subsequently cooled to 25° C. The agitator is then switched off and the emulsion left to settle for one hour. Phase separation occurs. The bottom aqueous phase is drained off. 400 mL of an aqueous 0.7% H$_2$SO$_4$ solution are added to the organic phase and the emulsion stirred for 4 hours. After 4 h, the agitator is switched off, and phase separation occurs again within 1 hour. The aqueous phase is then drained off. The wash step is repeated again.

A clear, dark green product solution with approx. 2% Rh in 99% yield is obtained.

The overall chlorine content is determined by means of a chlorine analyzer and is 1300 ppm (in relation to rhodium). The sodium content is determined per ICP-OES; the sodium content is <500 ppm (in relation to rhodium). The UV/VIS spectrum indicates an absorption band of 0.748 intensity at 597 nm.

Comparative Example 4: Preparation of Rhodium (III) 2-Ethylhexanoate in Texanol from Rh-Chloride Hydrate, Pursuant to U.S. Pat. No. 4,845,306 A1

32 g sodium hydroxide (10.3 eq., 99%, Merck) are dissolved in 400 mL DI water in a 1 L double jacket reactor while stirring. After cooling to room temperature, 78.4 g 2-ethylhexanoic acid (98%, Oxea) are slowly added drop by drop.

Meanwhile, 8 g rhodium in the form of approx. 39 g Rh(III) chloride hydrate (Umicore Product No. 68.2562.1138; Rh content 39.5 wt %) are dissolved in 360 mL DI water while stirring and then added to the sodium ethylhexanoate solution at room temperature within 15 minutes by means of a dropping funnel. The reaction mixture is heated to T$_{internal}$: 95° C. A yellow sediment of rhodium hydroxide precipitates. The conversion to product does not take place.

The invention claimed is:
1. A method for the preparation of a solution of rhodium (III) 2-ethylhexanoate, comprising the steps
   a) preparing an aqueous solution of an alkali salt of 2-ethylhexanoate by adding 2-ethylhexanoic acid to an aqueous alkali hydroxide solution at room temperature in a first reaction vessel, wherein the molar ratio of 2-ethylhexanoic acid to alkali hydroxide is 1.0:1.0 to 1.1:1.0 (mol/mol);
   b) providing a rhodium (III) precursor selected from rhodium (III) chloride hydrate, rhodium (III) chloride aqueous solution, and rhodium (III) nitrate aqueous solution, as well as mixtures thereof, in a second reaction vessel;
   c) mixing the aqueous solution of the alkali salt of 2-ethylhexanoate and the aqueous solution of the rhodium (III) precursor at an internal temperature of the reaction vessel of 20-30° C. to obtain a mixture;

d) heating of the mixture from step c)
to an internal temperature of the reaction vessel of 80-90° C., if the Rh(III) precursor is Rh(III) chloride aqueous solution or Rh(III) chloride hydrate, or
to an internal temperature of 80-100° C., if the Rh(III) precursor is Rh(III) nitrate aqueous solution, to obtain a suspension;
e) cooling of the suspension from step d) while stirring
to an internal temperature of 40-50° C., if the Rh(III) precursor is Rh(III) chloride aqueous solution or Rh(III) chloride hydrate, or
to an internal temperature of 55-65° C., if the Rh(III) precursor is Rh(III) nitrate aqueous solution,
f) adding an alcohol that is immiscible with water, a carboxylic acid that is immiscible with water, or a mixture thereof, while stirring,
g) stirring for 30 minutes to 3 h,
h) cooling to room temperature and leaving the resulting emulsion to settle,
i) draining off the bottom, aqueous phase, and
j) washing the top, product-containing organic phase with aqueous mineral acid, if the Rh(III) precursor in the step contains at least one of rhodium (III) chloride hydrate or rhodium (III) chloride aqueous solution.

2. The method according to claim 1, wherein the mixing of the aqueous solution of the alkali salt of 2-ethylhexanoate and the aqueous solution of the rhodium (III) precursors in accordance with step c) takes place discontinuously, wherein the solution of the rhodium (III) precursor is introduced first, and then the aqueous solution of the alkali salt of sodium 2-ethylhexanoate is added.

3. The method according to claim 1, wherein the alkali hydroxide in step a) is NaOH.

4. The method according to claim 1, wherein, in step f), the alcohol or the carboxylic acid is selected from 2-ethylhexanol, 2-ethylhexanoic acid, and texanol.

5. The method according to claim 1, wherein the aqueous mineral acid is sulfuric acid, nitric acid, or phosphoric acid.

* * * * *